United States Patent [19]

Lindstedt et al.

[11] Patent Number: 5,709,882

[45] Date of Patent: Jan. 20, 1998

[54] PHARMACEUTICAL FORMULATIONS CONTAINING A PHARMACOLOGICALLY ACTIVE IONIZABLE SUBSTANCE AS WELL AS A PROCESS FOR THE PREPARATION THEREOF

[75] Inventors: Bengt Magnus Lindstedt; Per Johan Gunnar Lundberg, both of Mölndal, Sweden

[73] Assignee: Astra Aktiebolag, Sodertalje, Sweden

[21] Appl. No.: 216,028

[22] Filed: Mar. 22, 1994

Related U.S. Application Data

[62] Division of Ser. No. 802,325, Dec. 4, 1991.

[30] Foreign Application Priority Data

Dec. 7, 1990 [SE] Sweden .................................. 9003903

[51] Int. Cl.⁶ .................. A61K 9/26; A61K 9/10; A61K 9/22
[52] U.S. Cl. .................. 424/469; 424/488; 424/486; 424/468

[58] Field of Search .................. 424/78.1, 426, 424/486, 484, 465, 469, 470, 483, 487, 501, 78.12

[56] References Cited

U.S. PATENT DOCUMENTS

| 5,032,393 | 7/1991 | Douglas et al. | 424/78.13 |
| 5,149,523 | 9/1992 | Lundberg et al. | 424/78.1 |

OTHER PUBLICATIONS

L. C. Feely and S. S. Davis, Intern'l J. Pharm 44 (1988) 131–139.

Primary Examiner—Edward J. Webman
Attorney, Agent, or Firm—White & Case

[57] ABSTRACT

A preparation of a pharmacologically active ionizable substance, wherein active substance is ionically complexed to an ion-exchanger resin, which is embedded in a hydrophilid eroding matrix as well as a process for the manufacture thereof.

15 Claims, 4 Drawing Sheets

Release of metoprolol at pH 7.5 from tablets of Example 1.

□ Complex with Dowex 50W-X4
── 0.61*(time)**0.92
△ Succinate salt
── 4.61*(time)**0.61

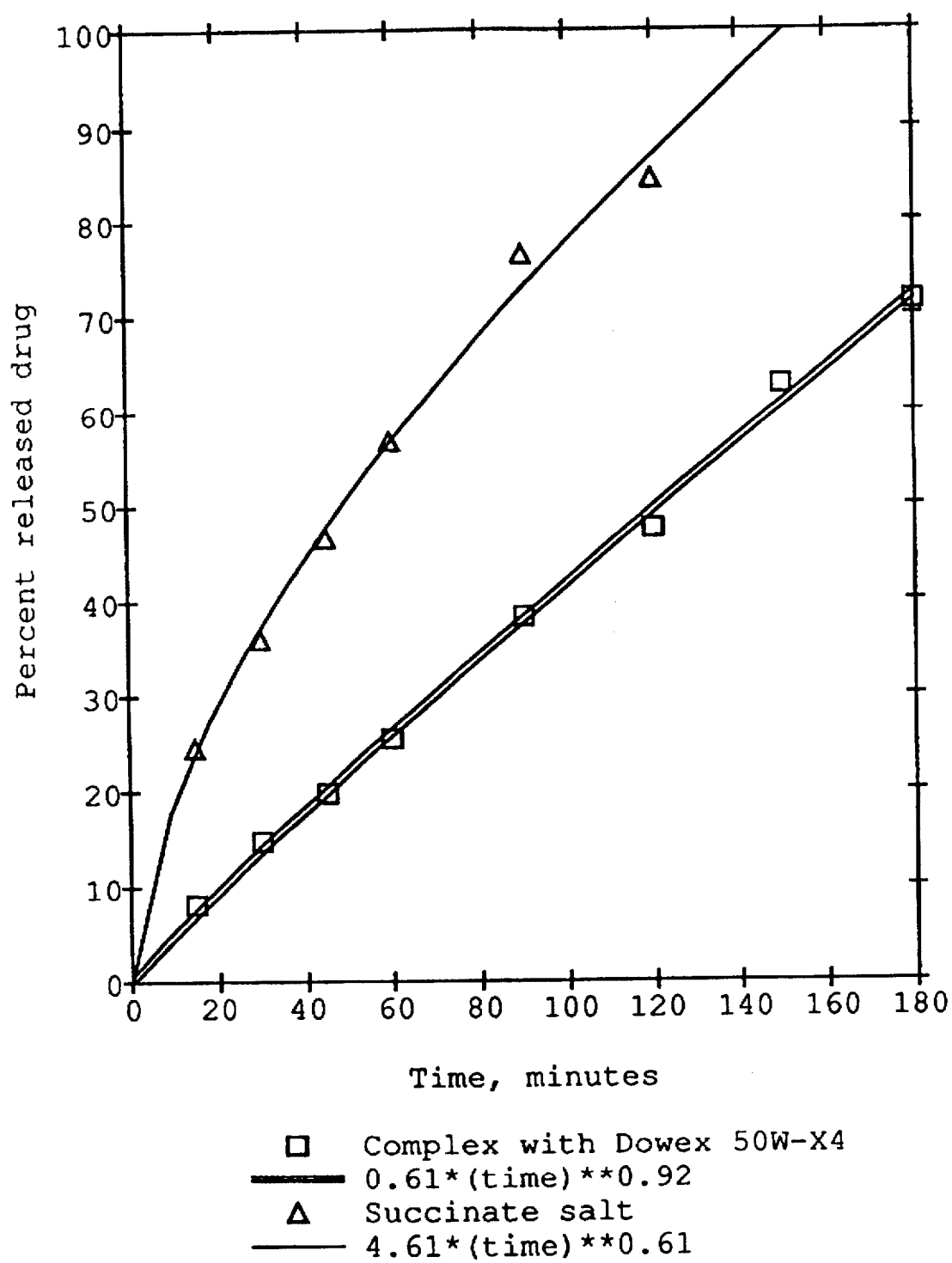
Figure 1. Release of metoprolol at pH 7.5 from tablets of Example 1.

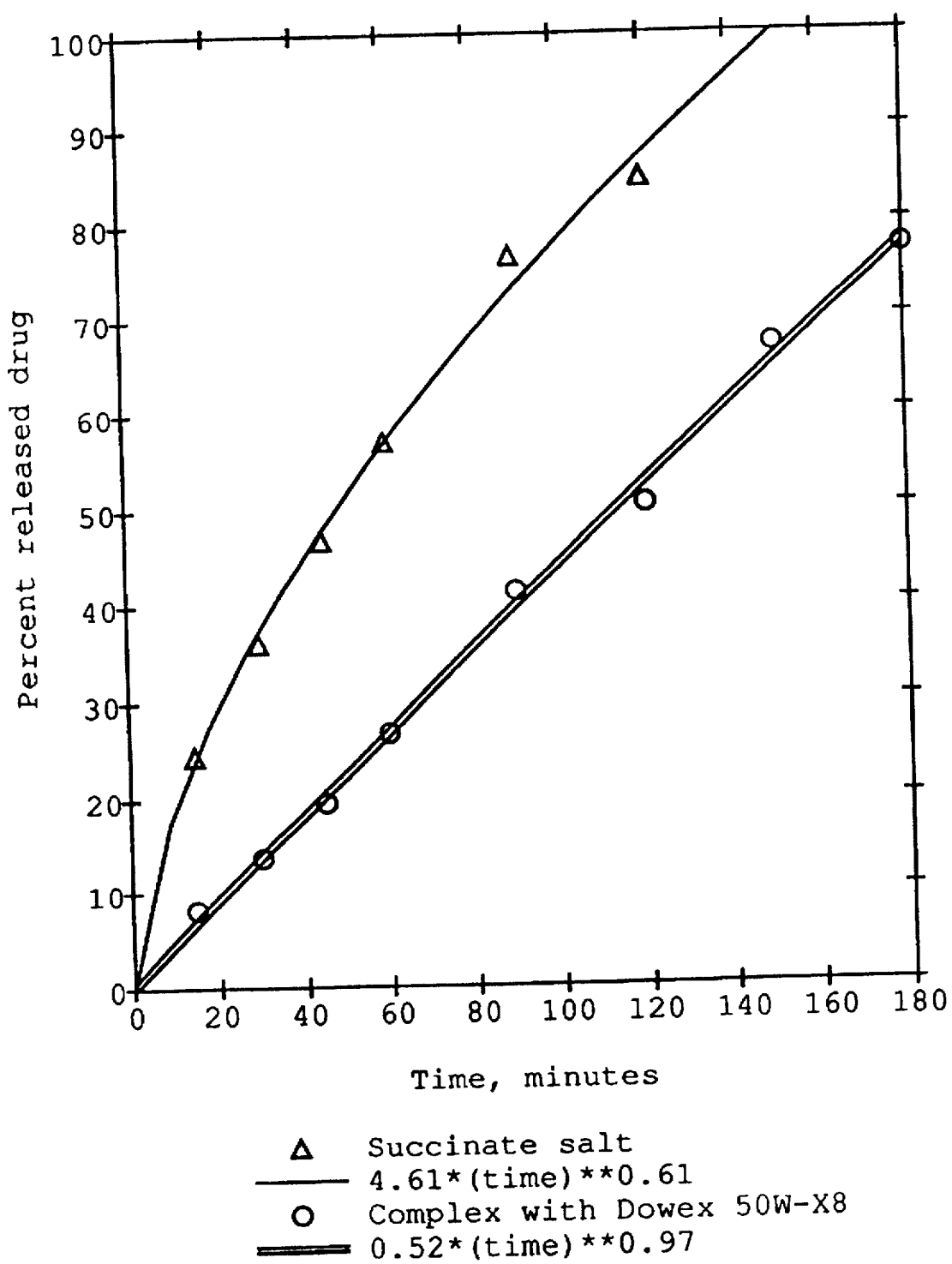
Figure 2. Release of metoprolol at pH 7.5 from tablets of Example 2.
△ Succinate salt
— 4.61*(time)**0.61
○ Complex with Dowex 50W-X8
═ 0.52*(time)**0.97

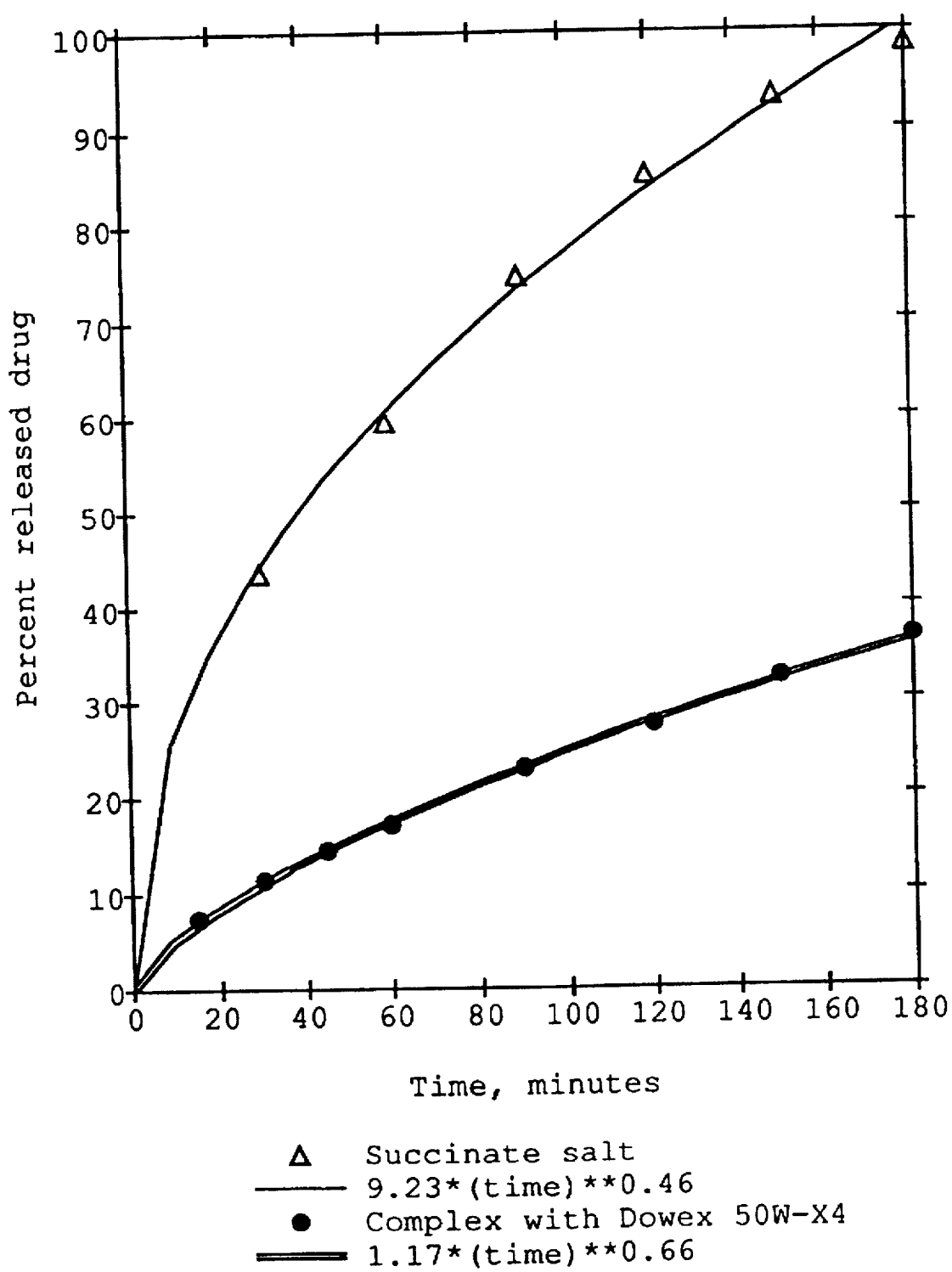
Figure 3. Release of metoprolol at pH 7.5 from tablets of Example 4.

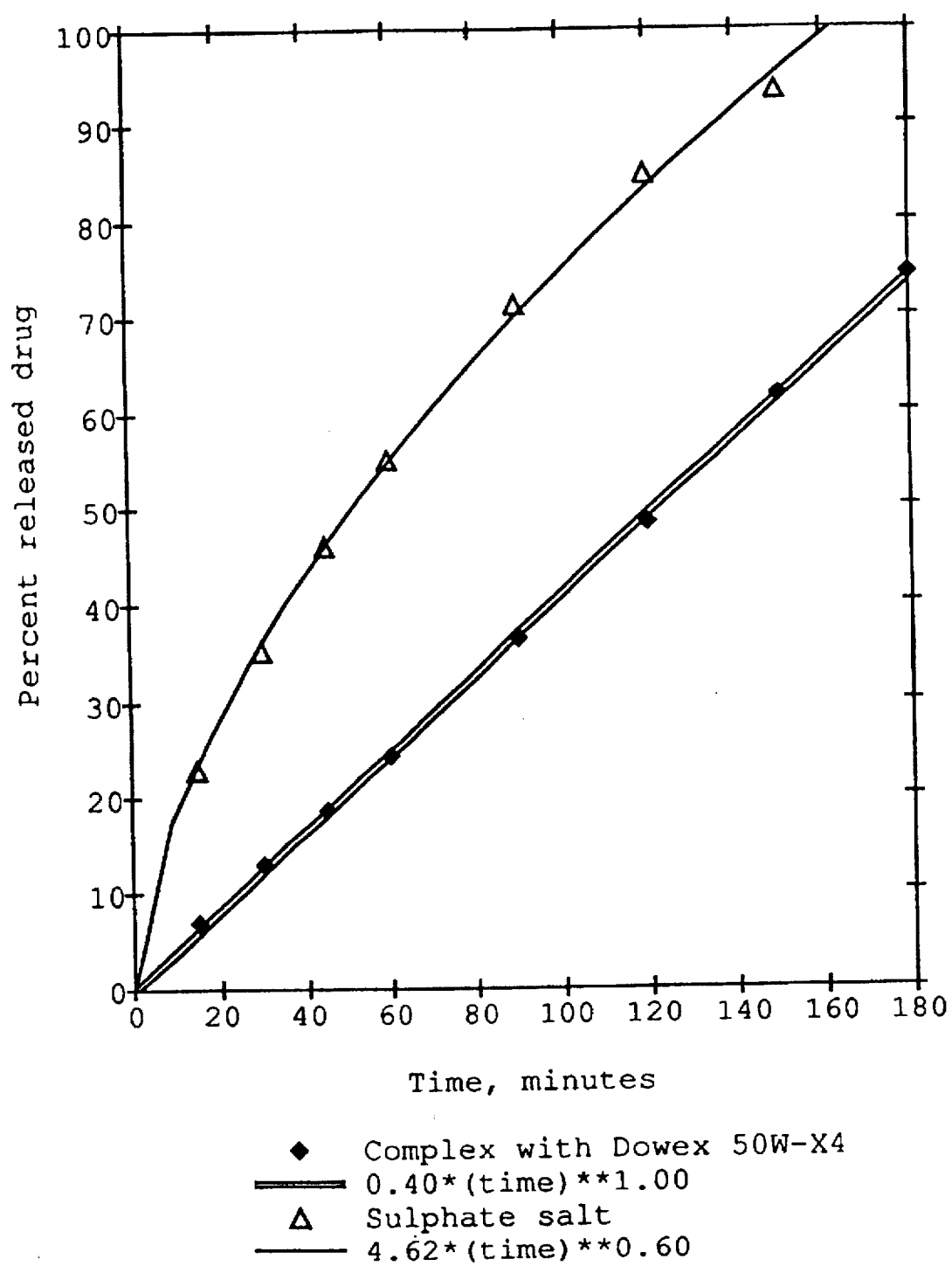
Figure 4. Release of terbutaline at pH 7.5 from tablets of Example 6.

5,709,882

PHARMACEUTICAL FORMULATIONS CONTAINING A PHARMACOLOGICALLY ACTIVE IONIZABLE SUBSTANCE AS WELL AS A PROCESS FOR THE PREPARATION THEREOF

This application is a divisional of application Ser. No. 07/802,325, filed on Dec. 4, 1991.

FIELD OF THE INVENTION

The present invention is directed to pharmaceutical formulations and their manufacture. One or more pharmacologically active substances are incorporated into the new formulations in order to be released over a desired period of time and, at the same time the dependence of the release rate on the fraction of substance remaining in the formulation, is minimized.

BACKGROUND OF THE INVENTION

Pharmaceutical preparations based on eroding, hydrophilic matrices, showing extended release properties, have been described for pharmacologically active substances of low and high water solubility. The release may be described by a simple exponential function, $$M(t)/M(\infty) = k \cdot t^n \qquad (1)$$

where n reflects the basic kinetics of the release (Ritger and Peppas, J. Contr. Rel. 5 (1987) 23–26). The most beneficial situation is when the release rate is totally independent of the fraction of substance remaining in the formulation that is n=1.

Active substances showing low water solubility have successfully been formulated into hydrophilic, eroding matrices. This has been described in U.S. Pat. No. 4,803,081, which shows favourable release kinetics. The same technique applied on substances of higher water solubility, such as metoprolol succinate, do not give the same beneficial release kinetics. This has limited the medical usefulness of this pharmaceutical principle.

Attempts have been made to improve the release kinetics of the hydrophilic eroding matrix, by using special geometrical arrangements, or introducing a gradient in drug concentration, of the formulations (P. I. Lee, Proc. Int. Symp. Contr. Rel. Bioact. Matr., 15 (1988) 97–98). It has also been proposed to restrict the access of water to the eroding matrix by applying coatings on selected surfaces, which raised the kinetic exponent n in Equation 1 (P. Colombo et al Int J Pharm., 63 (1990) 43–48). Probably none of these concepts has reached the open market, as the complicated manufacturing processes will make the products comparably expensive.

The technique to complex pharmacologically active substances to ionizable, crosslinked polymer particles (ion-exchange resins) is well known (A. T. Florence and D. Attwood, Physiochemical Principles of Pharmacy, Macmillan Press, London, 1982, 297–300, GB Pat 907,021 (1962)). The release of active substance can be controlled by varying the crosslinking density and particle size of the resin. The release rate is, however, depending on the fraction substance remaining in the particles. The complex has also been coated to further reduce the release rate (U.S. Pat. No. 4,221,778 (1980)). To reach an improvement in the overall release kinetics pellets with different coatings have to be mixed.

It has been suggested to use ion-exchange resins to reduce the release rate from hydrophilic matrices (L. C. Feeley and S. S. Davis, Int. J. Pharm. 44 (1988) 131–139). The pure resins were mixed with a pharmacologically active substance as a salt and a gel-forming polymer, a high viscosity hydroxypropyl methylcellulose (HPMC). No complex was, however, formed per se and the effect of the ion-exchange resin was only a reduction in the release rate.

GB 2 218 333 describes a preparation containing one active ingredient, namely ranitidine together with a synthetic cation exchange resin. Hydroxylpropyl methylcellulose may be added and is in that case used as a granulating additive and does not control the release rate.

EP 241 178 describes a pharmaceutical composition comprising one or more therapeutically active ingredients dispersed in a carrier. In this case no complex is formed.

EP 338 444 describes a composition containing azelastin which may be bound to a cation exchange resin. It has however not been proposed that a hydrophilic eroding matrix should be added.

EP 195 643 describes release by diffusion through a gel-forming layer in a transdermal preparation. Also a salt must be added to the composition in order to make the composition suitable for use.

BRIEF DESCRIPTION OF THE INVENTION

Brief Description of the Drawings

FIG. 1 compares the release kinetics of metoprolol in the formulation of Example 1 with that in the formulation of Reference Example 1.

FIG. 2 compares the release kinetics of metoprolol in the formulation of Example 2 with that in the formulation of Reference Example 1.

FIG. 3 compares the release kinetics of metoprolol in the formulation of Example 4 with that in the formulation of Reference Example 4.

FIG. 4 compares the release kinetics of terbutaline in the formulation of Example 6 with that in the formulation of Reference Example 6.

Active substances, available as dissociated ions, are complexed to insoluble, oppositely charged polymers, such as an ion-exchange resin. The particles formed, the complex, are embedded into a hydrophilic eroding matrix. Surprisingly, the release kinetics obtained were more beneficial, showing a higher value of the exponent n (Equation 1) than for the ordinary salt, base or acid.

DESCRIPTION OF THE INVENTION

The new preparations defined above give an even release of the active substance with high solubility in water. The different ingredients in the preparation are defined more in detail in the following:

Active substances are defined as compounds, which give a pharmacological effect when administered to humans or animals. To be useful in the present invention the substance must be available as dissociated ions. Therefore substances like glucose cannot be used. Instead bases, acids or amphoteric substances can be used.

It is preferable to use an active substance, which has a solubility greater than 10 mg/ml in water.

The ion-exchange resin has to be matched to the active substance and its physicochemical properties. Weak bases are best complexed with strong acid exchangers like sulphonic acids. These are often based on polystyrene crosslinked with divinylbenzene, and marketed under trademarks Resonium, Amberlite and Dowex.

The active substances may be used in the process as a salt or free base. The resin may be used in the acid form or as a salt of a suitable cation, such as sodium.

Stronger bases can be complexed to ion-exchange resins of lower acidity, such as crosslinked poly (acrylic acid) or styrene-divinylbenzene modified to contain carboxylic groups. It is also possible to use the mentioned sulphonic acid ion-exchangers.

Acids may be complexed with crosslinked polystyrene with quarternary amines, or other basic anion-exchangers. The acids may be used as free acids or suitable salts. The anion-exchanger may be used as base, with a hydroxylic ion on every amine, or a salt of a suitable anion, such as chloride.

The hydrophilic eroding matrix may consist of a polysaccharide. The hydrophilic matrix to more than 10% consists of a polysaccharide or a derivative thereof. Especially useful are derivatised celluloses such as methylcellulose (MC), hydroxypropyl metylcellulose (HPMC), both marketed under the tradenames Metolose and Methocel, and ethylhydroxy ethylcellulose (EHEC). We have found a grade HPMC, Metolose 60SH50 (viscosity 2% solution in water at 20° C. of approx. 50 mPas, 27.0–30.0% w/w methoxy groups and 7.0–12.0% w/w hydroxypropoxy groups) especially useful. Also a mixture of low and high molecular weight HPMC can be used. The use of different mixtures of HPMC gives according to known technique different release rates of the active ingredient. Cf J. Contr. Rel. 5 (1987) p. 159–172. The eroding matrix may also consist of synthetic hydrophilic polymers, such as polyvinylalcohol or polyvinylpyrrolidone.

Other useful materials are bioeroding polymers such as polyorthoesters and polyanhydrides, such as those described by Nguyen et al (J. Contr. Rel. 4 (1986) 9–16) and polyanhydrides (R. Langer et al, Proc. Int. Symp. Control. Rel. Bioact. Mater., 16 (1989) 119–120, 161–162, 338–339).

Processes for the Preparation of Tablets

Tablets are preferably prepared by embedding the complex into a hydrophilic eroding matrix by compression in an ordinary tablet press. Processes including solvent evaporation (casting), precipitation or polymerisation may also be used.

EXAMPLES

Example 1

1 kg Dowex 50W-X4, 200–400 mesh, was washed with 2 L 1M NaOH, 8 L deionized water, 2 L 0.1M NaOH, 8 L deionized water, 0.8 L methanol, 4 L water, 1.6 L 10% HCl and 12 L deionized water. The resin was dried overnight at 80° C., yielding 352 g resin with 8.5% moisture and 4.86 milliequivalents/g dry resin. 30.15 g resin was slurried in deionized water and a solution containing 44.06 g metoprolol succinate was added. After 10 minutes stirring, the resin was filtered on a sintered glass funnel. Another 8.01 g metoprolol succinate in water was added to the resin, and filtered off. The resin was rinsed with 2 L deionized water and dried overnight at 80° C., giving 64.44 g complex with a metoprolol content, determined spectrophotometrically at 274 nm, of 1.98 mmol/g. 1 g of the complex was carefully mixed with 3 g Metolose 60SH50 (viscosity 49 mPas in 2% water solution, 28.2% methoxy groups and 8.2% hydroxypropoxy groups) with a mortar and pestle. 400 mg of the mixture was filled by hand into 20 mm flat punches and compressed into tablets. The release of metoprolol was measured in a USP apparatus no 2 (paddle) at 50 rpm, with the tablets mounted in a stationary basket, in 1 L phosphate buffer at pH 7.5 and 37° C. The amount drug released was measured spectrophotometrically, for metoprolol at 274 nm.

Reference Example 1

1 g metoprolol succinate was mixed with 3 g Metolose 60SH50 (same lot as above) with a mortar and pestle. 400 mg of the mixture was filled by hand into 20 mm flat punches and compressed into tablets.

The fraction drug released is plotted versus time in FIG. 1. The exponent describing the release kinetics, defined in Equation 1, is evaluated using non-linear least square fitting available in the software package RS/1 (RTM). The exponent was found to be 0.92 for the tablet containing the complexed drug and 0.61 for the low molecular weight salt, the succinate.

Example 2

0.9 kg Dowex 50W-X8 200–400 mesh was treated similarly as in Example 1. The resin contained 5.10 mekv/g dry resin and 7.3% moisture. 30.02 g resin was treated with 44.06 g and 8.00 g metoprolol succinate in a similarly way as in Example 1. 57.76 g complex with 1.80 mmol/g was obtained. The tablets were manufactured and analyzed similarly as in Example 1 and the same reference was used. The release of the tablets is shown in FIG. 2. The release-describing exponent of Equation 1 was 0.97 for the tablets made according to this invention, compared to 0.61 for the reference tablet.

Example 3

1 g of the complex of Example 1 was mixed with 3 g Metolose 65SH50 (viscosity 47 mPas of 2% water solution, 27.3% methoxy groups and 4.2% hydroxypropoxy groups), compressed into tablets and analyzed similarly.

Reference Example 3

1 g metoprolol succinate was mixed with 3 g Metolose 65SH50 (same lot as above), compressed into tablets and analyzed with the method described in Example 1.

The kinetic exponent, defined in Equation 1, increased from 0.44 for the succinate salt to 0.68 for the complex.

Example 4

1 g of the complex of Example 1 was mixed with 3 g Methocel E4MCR (viscosity 4077 of 2% water solution, 30.0% methoxy groups and 8.6% hydroxypropoxy groups), compressed into tablets and analyzed similarly.

Reference Example 4

1 g metoprolol succinate was mixed with 3 g Methocel E4MCR (same lot as above), compressed into tablets and analyzed with the method described in Example 1.

The release kinetics of the inventive and reference formulations are shown in FIG. 3.

The exponent describing the kinetics of release increased from 0.46 (low molecular weight salt) to 0.66 (ion exchange resin complex).

Example 5

14.67 g Dowex 50W-X4 (from Example 1) was slurried in water. A water solution of 20.25 g lidocaine HCl.H$_2$O was added. After 10 minutes stirring the complex was filtered and washed with 4 L deionized water. After drying, the complex (24.84 g) contained 1.86 mmol/g, determined spectrophotometrically at 262 nm. Tablets were made according to Example 1 with the same lot of polymer and analyzed.

Reference Example 5

Tablets were also made from lidocaine-HCl.H$_2$O and Metolose 60SH50.

The kinetic exponent of Equation 1 was 0.95 for the tablet containing the complex, and only 0.58 for the low molecular weight salt.

Example 6

14.67 g Dowex 50W-X4 (from Example 1) was slurried in water. A water solution of 19.20 g terbutaline sulphate was added. After 10 minutes stirring the complex was filtered and washed with 4 L deionized water. After drying, the complex (25.57 g) contained 1.91 mmol/g, determined spectrophotometrically at 278 nm. Tablets were made according to Example 1 and analyzed.

Reference Example 6

Tablets were also made from terbutaline sulphate.

The release profiles of FIG. 4 demonstrate that the kinetic exponent was improved to 1.00 from 0.60 for the corresponding sulphate salt.

Example 7

13.70 g Dowex 50W-X4 (from Example 1) was slurried in water and filtered on a sintered glass funnel. The resin was washed with 1 L water containing 5% NaCl. The resin was further washed with 2 L deionized water. The resin was slurried in 100 mL water containing 20.05 g alprenolol HCl. After 10 minutes stirring the complex was filtered and washed with 4 L deionized water. After drying, the complex (27.15 g) contained 1.97 mmol/g, determined spectrophotometrically at 270 nm. Tablets were made according to Example 1 and analyzed.

Reference Example 7

Tablets were also made from alprenolol HCl.

The hydrochloric salt had an exponent of 0.63, significantly lower than the complex, 1.16.

Example 8

100 g Dowex 1X-2 was washed with 0.5 L 0.1M HCl, 1 L water, 200 mL methanol, 0.5 L water, 0.5 L 0.5M NaOH, 200 mL methanol, 0.5 L water, 1 L 5% NaCl followed by 2 L deionized water. The resin was dried at 80° C. overnight yielding approx. 60 g resin containing 11.5% water and 4.49 mekv/g dry resin. 6.68 g resin was treated with 100 mL 1M NaOH, filtered and washed with 2 L water and 2 lots of 200 mL ethanol and slurried in 200 mL ethanol. 3.46 g salicylic acid was added and the slurry was agitated for 9 hours. The complex was filtered and washed with two lots of 200 mL ethanol and 2 L water, 6.25 g complex containing 19.5% salicylic acid, measured spectrophotometrically at 296 nm, was obtained after drying overnight. 1 g complex was mixed with 3 g Metolose 60SH50 and tablets were prepared according to Ex. 1.

Reference Example 8

1 g salicylic acid was mixed with 3 g Metolose 60SH50 and compressed to tablets by the method described in Ex. 1.

The release curves were fitted to Equation 1, giving an exponent of 0.56 for the acid and 0.96 for the complex.

We claim:

1. A pharmaceutical composition for extended release of a pharmaceutically active ionizable substance comprising an ionic complex of an active ionic substance with an oppositely charged ion-exchange resin; the ionic complex being embedded in a hydrophilic eroding matrix consisting of 100% to 10% by weight of a derivatized cellulose and 0% to 90% by weight of a synthetic polymer; the hydrophilic eroding matrix being proportioned to the complex so as to effect a linear release of the active substance.

2. The pharmaceutical composition according to claim 1, wherein the hydrophilic matrix is hydroxypropyl methylcellulose (HPMC).

3. A preparation according to claim 1 wherein the active substance is a base and the resin is a cation-exchanger.

4. A process for the manufacture of a pharmaceutical composition according to claim 1 comprising the steps of:
   (a) complexing the active substance to an oppositely charged ion-exchange resin in water or ethanol so as to form an ionic complex;
   (b) embedding the dry resulting complex into a hydrophilic eroding matrix consisting of 100% to 10% by weight of a derivatized cellulose and 0% to 90% by weight of a synthetic polymer so as to form a dry mixture having an approximate ratio of 1:3 of the ionic complex to the hydrophilic matrix; and
   (c) shaping the resulting mixture into tablet form.

5. A pharmaceutical composition for extending release of an active ingredient comprising:
   (a) an ionizable active ingredient;
   (b) an ion-exchange resin which forms an ionic complex with the active ingredient; and
   (c) a hydrophilic eroding matrix consisting of 100% to 10% by weight of a derivatized cellulose and 0% to 90% by weight of a synthetic polymer wherein the ionic complex is embedded at an appropriate weight ratio of about 1 part of the ionic complex to 3 parts of the hydrophilic matrix.

6. The pharmaceutical composition according to claim 1 or 5 wherein the active ionizable substance has a solubility greater than 10 mg/ml.

7. An improved oral pharmaceutical composition effective for the extended release of a pharmacologically active substance from the composition containing an ionizable active substance ionically complexed with an ion-exchange resin in water, the ionic complex being embedded after drying in a hydrophilic erodible matrix consisting of 100% to 10% by weight of a derivatized cellulose and 0% to 90% by weight of a synthetic polymer, so as to effect the release rate of the active ingredient toward linearity; wherein the improvement of the composition comprises:
   a weight ratio of about 1:3 of the ionic complex to the hydrophilic erodible matrix.

8. An oral pharmaceutical composition for the extended release of a water soluble active ingredient comprising:
   (a) an ionizable water soluble active ingredient;
   (b) an ion-exchange resin which forms an ionic complex with the active ingredient in water; and
   (c) a dry hydrophilic erodible matrix consisting of 100% to 10% by weight of a derivatized cellulose and 0% to 90% by weight of a synthetic polymer; wherein the ionic complex is embedded after drying in the hydrophilic matrix at a weight ratio of about 1 to 3 and where the extended release is approximately linear.

9. The composition of claim 8, wherein the hydrophilic erodible matrix is selected from the group consisting of hydroxypropylmethylcellulose, methylcellulose, polyvinylalcohol, polyvinylpyrrolidone, polyorthoester, polyanhydride, and a mixture thereof.

10. A pharmaceutical composition for extended even release of a pharmacologically active ionizable substance comprising an ionic complex of an active ionic substance with an oppositely charged ion-exchange resin; the ionic complex being embedded in a hydrophilic eroding matrix consisting of hydroxypropylmethyl cellulose containing 27–30% methoxy groups and 7–12% hydroxypropoxy groups; the hydrophilic eroding matrix being proportioned to the ionic complex so as to effect an extended even release of the active substance.

11. A process for the manufacture of a pharmaceutical composition according to claim 9 comprising the steps of:
   (a) complexing the active substance to an oppositely charged ion-exchange resin in water or ethanol so as to form an ionic complex;
   (b) drying and embedding the ionic complex into a hydrophilic eroding matrix consisting of hydroxypropylmethyl containing 27–30% methoxy groups and 7–12% hydroxypropoxy groups cellulose so as to form a dry mixture having an approximate weight ratio of 1:3 of the ionic complex to the hydrophilic matrix; and
   (c) shaping the resulting mixture into tablet form.

12. The process according to the claim 4 or 11 wherein the ionic complex is rinsed with a suitable solvent so as to remove unbound active substance.

13. The composition according to anyone of the claims 1, 3, and 7–10, wherein the ionic complex is essentially devoid of unbound ionic active substance.

14. An oral pharmaceutical composition for the extended even release of a pharmacologically active substance from the composition comprising an ionizable active substance ionically complexed with an oppositely charged ion-exchange resin; the complex being embedded in a mixture with a hydrophilic erodible matrix consisting of hydroxypropylmethyl containing 27–30% methoxy groups and 7–12% hydroxypropoxy groups, the mixture being proportioned so as to effect the extended even release of the active substance.

15. The composition according to claim 14, wherein the mixture of hydrophilic matrix and ionic complex is compressed into the form of a tablet.

* * * * *